United States Patent [19]
Juranas

[11] Patent Number: 5,709,840
[45] Date of Patent: Jan. 20, 1998

[54] REACTOR FLASK

[75] Inventor: David L. Juranas, Bahama, N.C.

[73] Assignee: Tecan US., Inc., Research Triangle Park, N.C.

[21] Appl. No.: 584,660

[22] Filed: Jan. 11, 1996

[51] Int. Cl.$^6$ ....................... B01L 3/00
[52] U.S. Cl. ............ 422/99; 422/58; 422/100; 422/101; 422/102; 422/103; 422/104; 436/167; 436/177; 210/808
[58] Field of Search ............... 422/58, 99, 100, 422/101, 102, 103, 104; 436/167, 177; 210/798, 808

[56] References Cited

U.S. PATENT DOCUMENTS

| Re. 35,316 | 8/1996 | Negersmith et al. | 210/798 |
|---|---|---|---|
| 4,168,394 | 9/1979 | Yeuy | 174/151 |
| 4,482,159 | 11/1984 | Ishitani et al. | 277/3 |
| 4,605,536 | 8/1986 | Kuhnert et al. | 422/99 |
| 4,787,988 | 11/1988 | Bertoncini et al. | 210/808 |
| 4,806,316 | 2/1989 | Johnson et al. | 422/100 |
| 5,045,193 | 9/1991 | Pinon et al. | 210/232 |
| 5,061,450 | 10/1991 | Aoyagi | 422/101 |
| 5,064,542 | 11/1991 | Negersmith et al. | 210/798 |
| 5,133,561 | 7/1992 | Hattori et al. | 277/3 |
| 5,460,973 | 10/1995 | Schrader | 436/167 |
| 5,552,294 | 9/1996 | Thorne | 435/7.32 |
| 5,578,455 | 11/1996 | Tosa et al. | 435/7.32 |
| 5,578,549 | 11/1996 | Gordon et al. | 135/29 |

OTHER PUBLICATIONS

Promotional Brochure by Tecan entitled "A new concept in Robotic Sample Processing", Jan., 1995.

Primary Examiner—Harold Y. Pyon
Attorney, Agent, or Firm—Olive & Olive, P.A.

[57] ABSTRACT

A first aspect of the invention involves placing a pair of parallel, spaced apart sealing septa in each channel of a reactor block through which materials are added to or removed from a reactor flask such that the septa enclose a cavity within the channel. A hole is formed through the block to intersect the cavity and is connected to a source of low pressure, substantially non-reactive gas which acts to prevent materials from leaking through a hole in either septum. The reactor flask is formed of glass as a substantially conical chamber with a first tube and a second tube connected to the flask perpendicular to its axis. The second tube extends within the flask so that its interior end resides proximate the opposite interior surface of the flask. The second tube terminates in a glass frit being permeable to certain of the chemical materials in work and non-permeable to others so as to act as a filter. The two tubes are assembled into the holes in the reactor block and held in position with resilient O-rings forced into pressurized contact with an internally conical washer in each hole, supporting the reactor flask in a nominally horizontal orientation for operation.

14 Claims, 4 Drawing Sheets

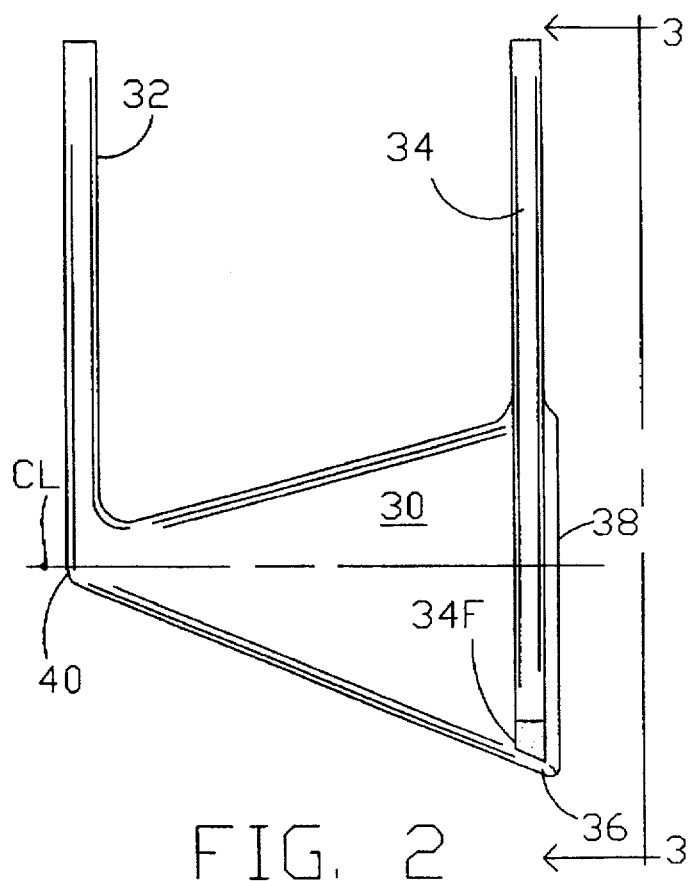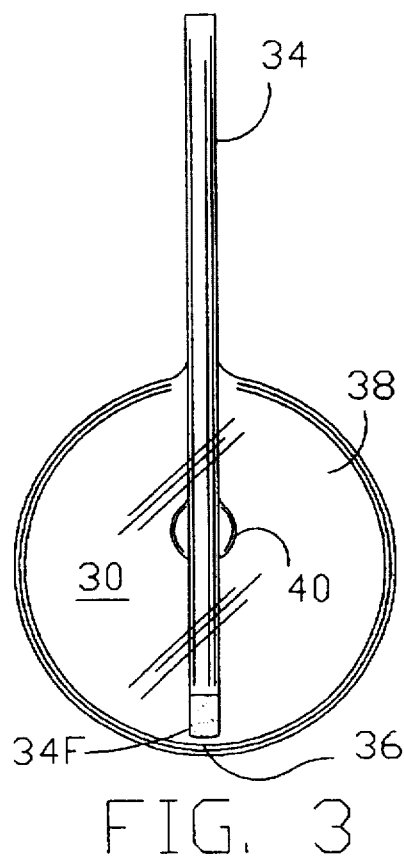

REACTOR FLASK

BACKGROUND OF THE INVENTION

1. Field of the Invention

This invention relates to the automatically mechanized combining of chemical components and the synthesis and evaluation of compounds therefrom, and more particularly to a reactor flask used therefor and transmission of ingredients into and out of such flasks.

2. Description of the Related Art

Contemporary chemical research and development involves the creation and evaluation of numerous chemical compounds from which a meager few emerge as ultimately successful commercial products. The classical portrait of a laboratory scientist selecting, mixing and, reacting chemical components and testing the resultant compounds has been largely replaced with modern, computerized machinery with robotic servers sequentially creating substantially all possible combinations to screen the multitudinous choices thoroughly. Automated synthesis has been acknowledged to be preferred in order to preclude accidentally missing an unobvious, but beneficial choice.

A particular system for selecting and combining ingredients, warming and agitating the mix and removing the resultant compound for evaluative testing is exemplified by GENESIS™ robotic sample processors, supplied by Tecan US, Inc. of Research Triangle Park, N.C., The GENESIS™ processor utilizes up to eight aspiration and injection tips mounted on a robotic arm. This sample processor is capable of transferring liquids to and from a multitude of reaction chambers and vials installed on the working surface of the instrument. The entire operation, including the washing of vessels between successive reaction cycles, is controlled by a programmed computer.

This automated process is primarily directed to the solid phase synthesis of peptides and medicinal compounds using solid supports (resins). The resins are typically small beads ranging in size from 10 μm to 100 μm in diameter which include reactive sites for the covalent bonding of reactant molecules. Resins are added as a dry powder or in a solvent-based slurry to individual reaction chambers. Through a series of building block additions and subsequent chemical reactions, the desired chemical compounds are synthesized. Excess reactants and by-products are removed from the reaction chambers by aspirating the liquids through a filtering frit, leaving the larger resin beads with covalently bonded molecules within the chamber. After the desired molecule is thus synthesized, it is cleaved off the resin bead by chemical reactions, leaving the desired molecule in solution. The isolated compound is then removed from the chamber through the filter frit, leaving the resin bead in the chamber.

In the prior art, the reaction chamber is typically a cavity formed within a Teflon reactor block. A sealing membrane, or septum, is affixed to the block to seal the top of the chamber. The bottom of the chamber is covered with a glass frit that allows the solvent to pass through to the bottom of the chamber, leaving the resin within. A tube is attached to each chamber below the glass frit extending upwardly to a height comparable to the top of the chamber and back down to the bottom of the block. The serpentine tubing serves as a trap, or valve, to prevent the solvent from draining out of the chamber. In the prior art, a transverse channel is machined into the block to connect a common pressurized inert gas source to all the chambers. When gas is introduced and a sufficient amount of pressure is applied (2–3 lb/in$^2$), the liquid in the reaction chamber is forced through the frit and lower tubing, simultaneously evacuating all chambers of liquid, but leaving the resin within the chamber.

The known apparatus described has the drawback that the chemicals are in constant contact with the material of the block. The block materials of choice have been either stainless steel or TEFLON®(E.I. duPont De Numours Company) polytetrafluoroethylene resin, each having certain limitations. While stainless steel is substantially impervious to chemical attack, it is quite heavy and it conducts heat well. TEFLON® is fairly chemically inert, but will be affected by certain chemicals. With either material, the cleaning of tubing and machined holes is difficult and unreliable.

Beside the cleaning problem discussed above, in order to maintain purity in the reactor vessel, the ingredients must be added from clean sources and the vessel sealed before and during the reaction cycle. A sealing membrane, or septum, typically covers the entrance to the inlet and outlet tubes. Instillation tips used must penetrate the septum, and the septum must be chemically inactive and sealable. Although a natural latex septum would provide an adequate seal, latex is not sufficiently impervious to chemical attack for general use. A better, and commonly used, choice for chemical purity is a TEFLON®coated-silicone rubber composite sheet. The silicone provides the resiliency needed for sealing and the TEFLON® provides the chemical inactivity. However, the TEFLON®is not a perfect choice for chemical resistance, as noted above, and the silicone does not close after penetration as well as a latex sheet. Since TEFLON®does exhibit some reactivity to the chemical agents, it is important to minimize the exposed surface area of the septum to the chemicals in the reaction chamber and remove the septum a distance from the reactive solvents.

It is therefore an object of this invention to provide a reactor flask which allows the instilling and removal of chemical ingredients through passages totally free of contamination.

It is a further object of this invention to provide a reactor flask which permits thorough and efficient cleaning between reaction cycles.

It is an additional object of this invention to provide an improved seal for the inlet and outlet tubes of such reaction flask to prevent leakage.

It is an additional object of the invention to provide a reactor flask which permits evacuation of resultant chemical products from each such flask independent of other such flasks.

Other objects and advantages will be more fully apparent from the following disclosure and appended claims.

SUMMARY OF THE INVENTION

The invention provides an improved reactor flask and an apparatus for sealing against leakage into or out of such vessel during chemical synthesizing. The vessel described is a horizontally disposed conical chamber with a pair of parallel inlet and suction tubes attached thereto for transfer of material. The suction tube intended for removal of materials terminates in a frit at a lowest portion within the vessel. The sealing arrangement requires a pair of penetrable septa surrounding a cavity in line with each inlet and suction tube with the cavity supplied with pressurized, non-reactive gas to prevent materials escaping through residual holes in the penetrated septa. The seal arrangement may be used with the reactor equipment of the prior art as well as that of the present invention.

BRIEF DESCRIPTION OF THE DRAWINGS

FIG. 2 is a side elevation view of a reactor cell of the present invention, comprising integral input and suction tubes.

FIG. 3 is an end elevation view of the reactor cell of FIG. 2 taken in the direction of line 3—3 of FIG. 2.

DETAILED DESCRIPTION OF THE INVENTION AND PREFERRED EMBODIMENTS THEREOF

Figure 1:
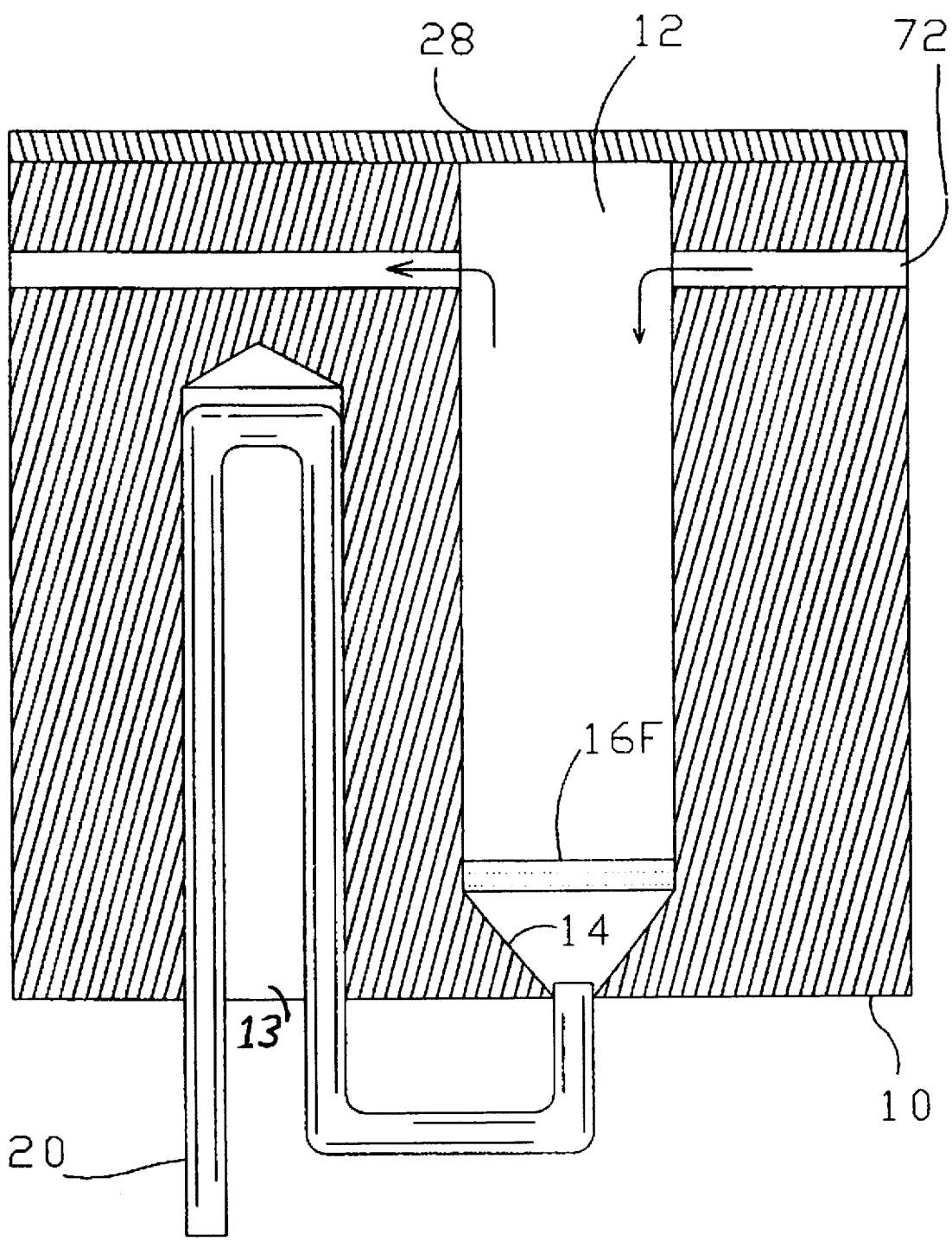
FIG. 1 is a side elevation view of a reactor block of the prior art in cross section into which is machined a reaction chamber with a drain tube mounted thereto.

The invention provides an improved embodiment of reactor blocks and reaction chambers for use in automated chemical synthesis over those known in the art. The apparatus of the prior art as discussed above is illustrated in FIG. 1 with its reactor block drawn in cross section for clarity. Reactor block 10 is formed with reaction chamber 12, drain cavity 14 and transverse gas channel 72. Channel 72 intersects each in a series of reaction chambers 12. Drain tube 20 is connected at one end to drain hole 14 and extends upward within hole 13 to the top of the operative portion of reaction chamber 12 and then back down, forming a trap or valve to prevent liquids from draining out of the reaction chamber. At the bottom of the chamber is a frit 16F which is formed by fusing glass beads together under heat and pressure. The frit is press-fitted into place to prevent movement of the frit and prevent the passage of resin around the frit. The top of the reaction block, including reaction chamber 12, is sealed with a penetrable septum 28.

In use, an injection needle (not shown) penetrates septum 28 and transfer the resin or chemical reactants into chamber 12, after which the needle is withdrawn. At the completion of the reaction time, a positive gas pressure is applied through channel 72 and the excess reactants or reactant products are forced through frit 16F, leaving the resin within chamber 12. As discussed above, because in the prior art the chemical compounds are in contact with the material of block 10 and drain tube 20, residue contamination as well as chemical reactions with the material of block 10 and drain tube 20 are possible. Septum 28 is also exposed to the chemicals within the chamber during agitation, resulting in possible cross reactions. The prior art design requires that all interconnected chambers through transverse channel 72 be drained at the same time, preventing the draining of individual chambers.

A first improvement of the present invention over the prior known apparatus is reactor cell 30 of the invention (FIGS. 2–3). Interior features are visible since cell 30 is preferably formed of clear glass. When viewed in side elevation in its operative orientation, reactor cell 30 appears as a horizontally disposed cone having a pair of parallel, straight tubes 32, 34 extending upwardly therefrom. Inlet tube 32 is sealingly connected to the body of reactor cell 30 adjacent its smaller end 40 so as to terminate at the point of entry of inlet tube 32 into reactor cell 30. Suction tube 34 is sealingly connected to the body of reactor cell 30 adjacent the larger end 38 of reactor cell 30 so as to terminate in glass frit 34F adjacent the lowest point 36 within reactor cell 30. Glass frit 34F is welded to close the lower end of suction tube 34 and serves to provide a permeable separation between the material in the conical portion of cell 30 and suction tube 34 and acts as a filter. Inlet tube 32 and suction tube 34 are made of glass in the preferred embodiment and reside in substantially mutually parallel orientations with their distal ends to terminating at substantially the same height above a horizontal center line CL of reactor cell 30. Glass frit 34F has a pore size of between 50–150 µm, preferably between 70–100 µm and is connected to the lower end of suction tube 34 by welding so as to require any material passing through suction tube 34 to first pass through frit 34F. The lower end of frit 34F is cut at an angle to draw fluid from the lowest point 36 in reactor cell 30.

As described above, reactor cell 30, including inlet tube 32 and suction tube 34 is entirely made of glass, thus being substantially impervious to a broad spectrum of chemical agents and being comparatively easy to clean. By providing a straight inlet tube 32 parallel to suction tube 34, reactor cell 30 may be installed in a reactor block so that the chemical components involved will only contact glass surfaces, as shown in FIG. 4.

Figure 4:
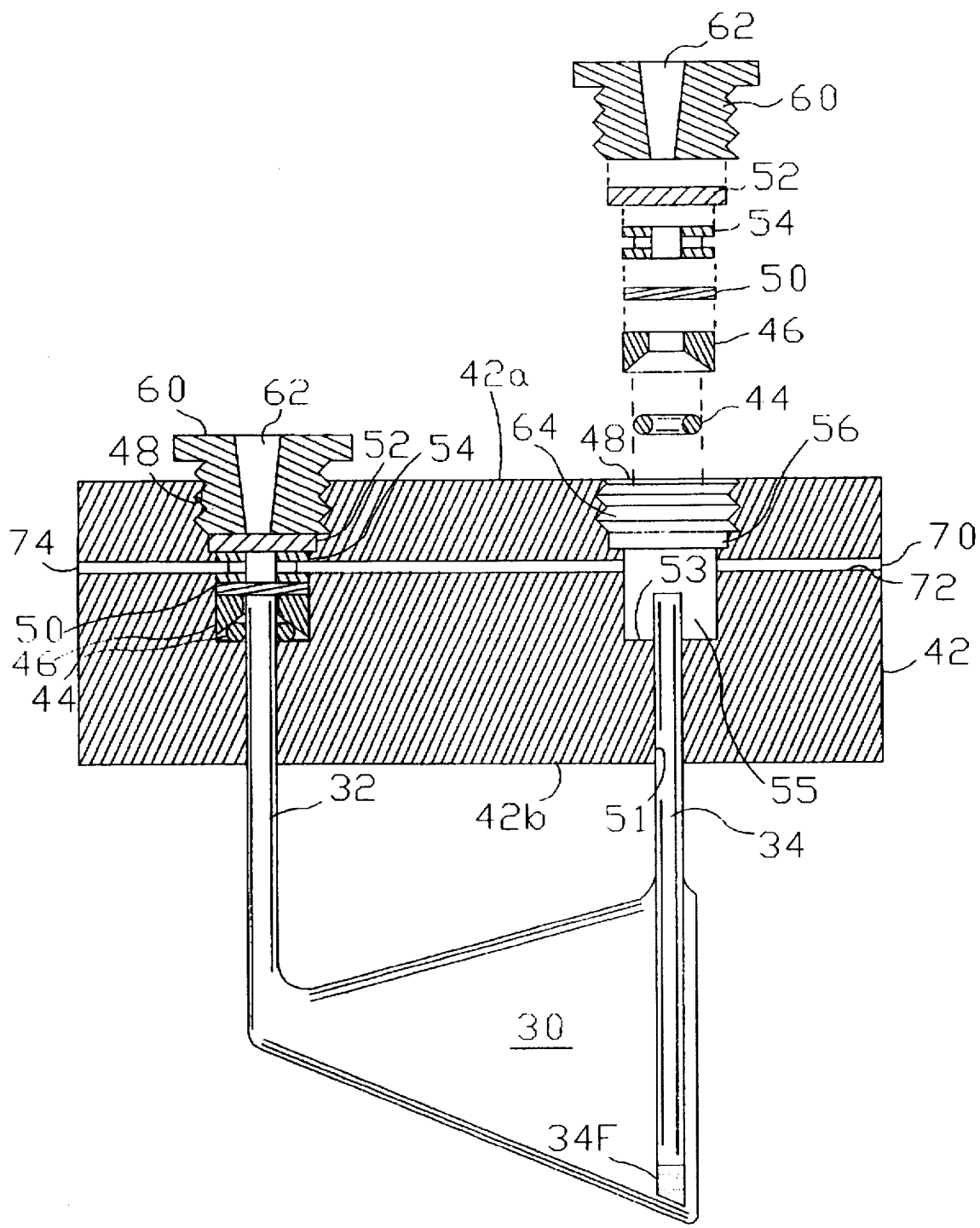
FIG. 4 is a side elevation partially exploded view of a reactor block of the invention in cross section with a reactor cell of the invention (not in cross section) operationally connected thereto.

A typical portion of a reactor block 42 to which a reactor cell 30 of the invention is mounted is shown in cross-sectional side elevation in FIG. 4. Block 42 is machined with a plurality of substantially parallel stepped passages 48 extending from upper surface 42a to lower surface 42b and spaced from one another to receive parallel tubes 32, 34. An advantage of reactor cell 30 having a pair of parallel tubes 32, 34 which each terminate the same distance from centerline CL is that chemicals added to or removed from cell 30 only contact glass surfaces, thus improving processing purity. Tubes 32 and 34 are of a length sufficient to insert into portion 55 of block 42. Typical stepped passage 48 has an upper end with threaded portion 64 which extends down to a shoulder 56. The intermediate portion 55 of passage 48 comprises a straight bore of a smaller diameter than threaded portion 64 which extends downward to a second shoulder 53. A lower portion 51 of passage 48 comprises a straight bore of a smaller diameter than intermediate portion 55 and extends through to the lower surface 42b of reactor block 42.

In assembly, inlet tube 32 and suction tube 34 of reactor cell 30 are inserted respectively in adjacent lower portions 51 of passages 48. A resilient annular sealing member 44, such as an "O" ring is placed over the upper end of each tube 32, 34. A pressure washer 46, being formed with an internal diameter somewhat larger than the outside diameter of tubes 32, 34 but smaller than the outside diameter of sealing member 44 is placed upon each sealing member 44. The lower portion of pressure washer 46 is formed with an internal conical cavity to contact sealing member 44 without contacting shoulder 53. When pressure is exerted on pressure washer 46, its internal conical cavity presses sealing member 44 against respective shoulder 53 and respective tube 32, 34 simultaneously, thus sealing the exterior of each tube 32, 34 to reactor block 42. A first penetrable sealing member, planar septum 50, such as is used in the system of the prior art discussed above, is placed on the flat upper surface of pressure washer 46.

Figure 6:
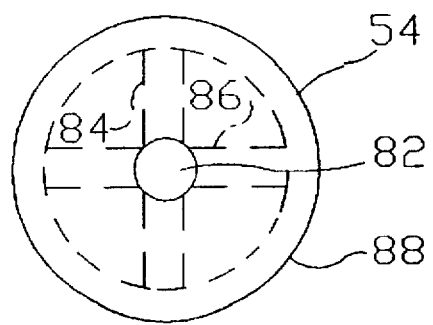
FIG. 6 is an enlarged top plan view of a spacer formed with gas flow channels for use in the apparatus of the invention and also show in FIGS. 4 and 5.

Spacer 54, shown in detail in FIG. 6, is assembled upon septum 50. Spacer 54 is formed as a cylindrical segment having an axially oriented central bore 82 and a pair of perpendicular diametrical bores 84, 86 formed so that bores 82, 84, 86 mutually intersect at the center of spacer 54. A circumferential channel 88 connects the respective outer end of each of bores 84, 86. A second penetrable sealing member, septum 52, somewhat larger in diameter than first septum 50 is placed onto spacer 54 so as to be vertically spaced from and rests on shoulder 56. Plug 60, having a conically formed entry 62 in its center, is adapted to engage threads 64 in passage 48. When screwed into position, plug 60 applies a downward force on each of the components placed in passage 48 to cause a sealing between each adjacent component, i.e., between second septum 52 and shoulder 56, and between sealing member 44, shoulder 53 and tube 32 or 34.

When a chemical is added to reactor cell 30 or a resultant compound is suctioned out, a hollow injecting needle (similar to that indicated by numbers 76, 78 in FIG. 5) is inserted through septa 50, 52. Upon completion of the addition or removal operation, the needle is extracted, leaving a small residual hole, as discussed above. Since the chemical reaction to be performed is aided by heating and agitating reactor block 42, carrying a plurality of reactor cells 30, a chance of leakage of fluid through the residual holes exists.

In the prior art reactor vial as depicted in FIG. 1, because of the substantially spherical form thereof, orbital agitation has been found to be needed to completely react the components. In the case of the reactor cell of the present invention with a horizontal axis of rotation, an oscillatory rocking motion has been found to be sufficient for reaction. The mechanism for orbital motion being more complex than a simple oscillator, the present invention is preferred for the mechanical simplicity of the agitator device required.

Reactor block 42 has a transverse channel 72 which extends from inlet 70 to exit 74 in the illustration. In practice, channel 72 intersects each passage 48 in the series of passages 48 in turn, with a flow-restrictive gas valve (not shown) at its ultimate exit 74. Channel 72 is located so as to be substantially level with the horizontally oriented cross holes 84, 86 in each spacer 54 so as to be open to upper septum 52 and lower septum 50. During operation of the reactor system, a gas having a low reactivity, such as nitrogen or argon, is maintained in channel 72 under a slight positive pressure. A preferred pressure in the present invention is between about 0.07–0.34 g/cm$^2$ (1–5 lb/in$^2$), preferably about 0.14 g/cm$^2$ (2 lb/in$^2$). The gas is thus able to prevent the escape of gas or liquid from reactor cell 30 through a residual hole in septum 50 or entry of gas or liquid from the atmosphere through a residual hole in septum 52. Since there is an individual inlet tube and suction tube for each chamber, liquids can be randomly removed from selected chambers without affecting the others. This greatly enhances the flexibility of the system. Lower septum 50 is also removed from direct contact with the chemicals in the reaction chamber during agitation and a much smaller surface area of septum 50 is exposed, further reducing the possibility of any possible cross reactions with septum 50.

Reactor cell 30 provides a total glass environment for any chemical ingredients involved. Therefore, the material of which reactor block 42 is made becomes less critical than in the prior art. It is anticipated that the material of the septa utilized in the apparatus of the invention will generally be similar to the TEFLON® and silicone composite sheet described above in reference to known septa. The material of which the plugs, spacers and pressure washers are made is left to the discretion of the designer of the particular system according to the chemical and thermal parameters of the system contemplated.

Figure 5:
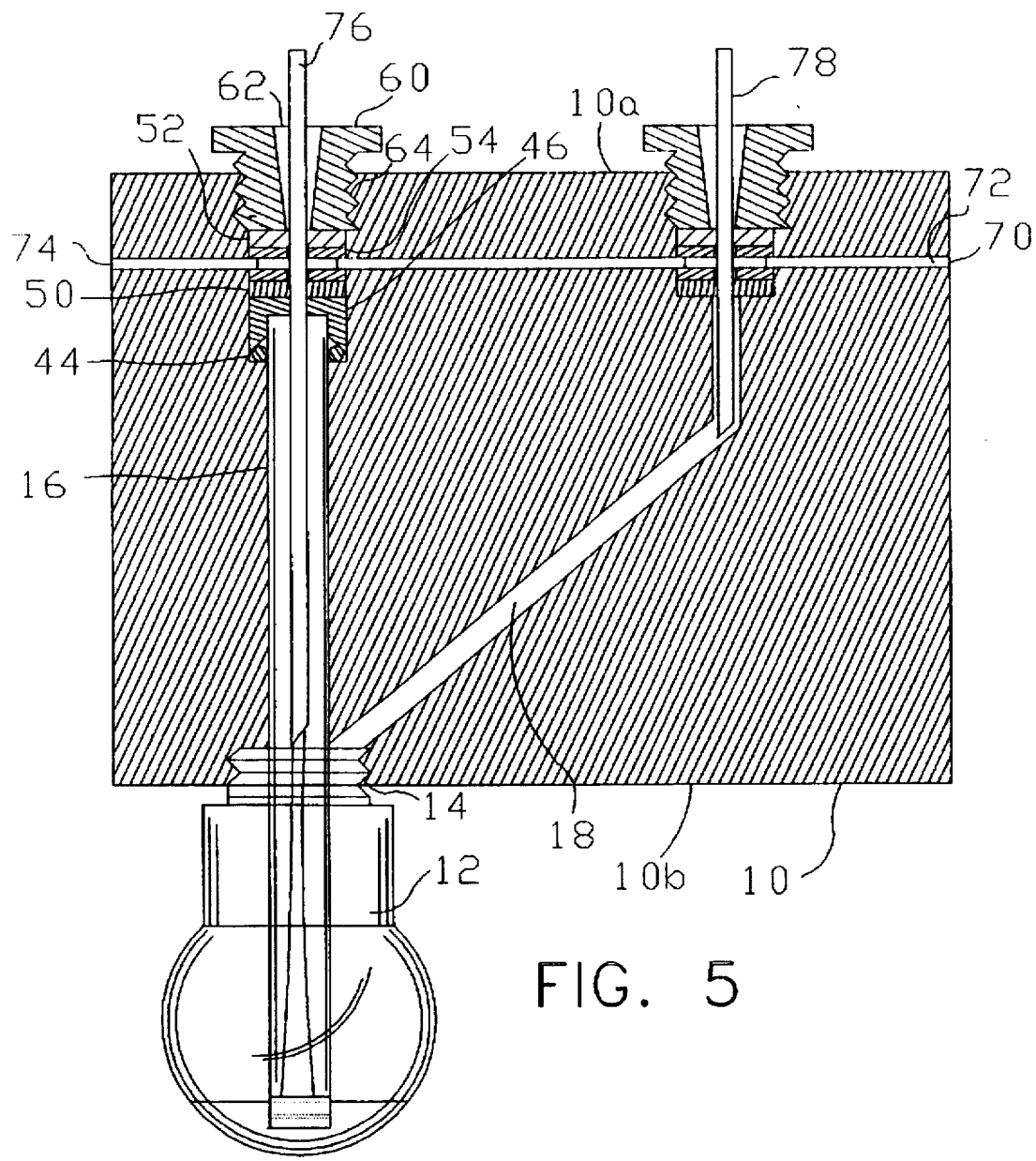
FIG. 5 is a side elevation view of a second embodiment reactor block of the invention in cross section with a reactor vial (not in cross section) having a suction tube mounted thereto and a supply and removal tip in each respective hole.

The positive pressure inert gas sealing system described in respect to FIG. 4 may be adapted to the apparatus of the prior art. Such an adaptation is shown in FIG. 5. A spherical vial 12 is screwed into a reactor block 10 with inlet channel 18 and suction tube 16 each extending from upper surface 10a to lower surface 10b. By the addition of pressurized gas channel 70–72–74, dual septa 50, 52 and spacers 54, a superior anti-leak seal is achieved in both inlet channel 18 and suction channel 16. A typical insertion hollow needle 78 is shown in position within inlet channel 18 to add material therethrough to vial 12. A suction hollow needle 76 is shown in position in suction tube 16 to remove material from vial 12 at the completion of processing.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. An apparatus for chemical synthesis comprising:
   (a) a reactor block having a pair of passages each extending from an upper block surface to a lower block surface;
   (b) a reactor flask formed with an upper portion releasably connected to said reactor block and in fluid communication with each of said passages;
   (c) each of said passages having a pair of substantially parallel penetrable sealing members in vertically spaced apart relation; and
   (d) means between said sealing members for preventing leakage of fluids escaping said flask through either of said passages after each said sealing member has been perforated.

2. The apparatus described in claim 1, wherein said reactor block has a channel which intersects each said passage, said channel being in fluid communication with a source of pressurized gas.

3. The apparatus described in claim 1, wherein said two passages in said reactor block converge to an intersection in fluid communication with said upper portion of said reactor flask when connected to said reactor block.

4. The apparatus described in claim 3, wherein said reactor block has a channel intersecting each said passage, said channel being in fluid communication with a source of pressurized gas.

5. The apparatus described in claim 1, wherein said passages in said reactor block are substantially parallel and said upper portion of said reactor flask has a pair of substantially parallel tubes connected to said reactor flask and configured to be received within said pair of passages.

6. The apparatus described in claim 5, further comprising a pair of annular sealing members adapted for securing each said tube within said respective passage and operative to seal each said tube to said reactor block.

7. The apparatus described in claim 6, further comprising a pair of pressure washers each having an axial bore larger than the respective said tube and having an internal conical cavity.

8. A method for performing automated chemical synthesis apparatus described in claim 1, comprising the steps of:
   (a) supplying a reactor flask having an inlet for adding selected chemical ingredients to said reactor flask and a suction tube for removing chemical products from said reactor flask;

(b) releasably connecting said reactor flask to a reactor block so that said inlet and said suction tube are each connected to a respective passage in said reactor block;

(c) sealing each said inlet and said suction tube with a resilient penetrable sealing member; and (d) providing a pressurized gas to be in contact with a surface of said sealing member distal from said reactor flask to prevent leakage of materials from said reactor flask.

9. The method described in claim 8, further comprising the step of providing a filter for filtering materials passing through said suction tube.

10. An apparatus for chemical synthesis, comprising:

(a) a reactor flask having a horizontal axis extending between a first flask end and a second flask end;

(b) a first straight tube sealingly connected to said reactor flask adjacent the first flask end and extending outward from said flask perpendicular to said axis;

(c) a second tube parallel to the first tube and sealingly connected to said reactor flask adjacent the second flask end with an outer end of said second tube extending outward from said reactor flask and an inner end of said second tube extending inward of said reactor flask; and (d) a filter positioned within said flask and fixedly connected to close said inner end of said second tube so as to require material passing through said second tube to pass through said filter.

11. The apparatus of claim 10, wherein said reactor flask is formed so that when said axis is substantially horizontal, said second end of said second tube resides at a low level relative to said axis.

12. The apparatus as claimed in claim 10, wherein said filter is formed with a nominal pore size of 70–100 μm.

13. An apparatus for sealing a tube in fluid communication with a block comprising;

(a) a resilient annular sealing member adapted for placement within a passage in said block and receiving an end of said tube within an opening of said sealing member;

(b) a pressure washer having a first planar surface, an axial bore perpendicular to said first surface and larger in diameter than said tube and a conical cavity formed in a second surface which is substantially parallel to said first surface, said cavity positioned to enclose said sealing member;

(c) a first resilient planar sealing member positioned adjacent said first surface;

(d) a spacer having opposed parallel planar surfaces and a periphery, an axial bore perpendicular to said planar surfaces, a diametral bore intersecting said axial bore, and a channel around said periphery and intersecting the ends of said diametral bore, said spacer positioned adjacent said first resilient sealing member;

(e) a second resilient planar sealing member positioned adjacent said spacer;

(f) a plug releasably attachable to said passage and adapted to apply pressure to said second planar sealing member, said spacer, said first planar sealing member, said pressure washer and said annular sealing member to seal the end of said tube within said passage; and (g) wherein the tube is a reactor flask having an inlet for adding selected chemical ingredients to said reactor flask and a suction.

14. The apparatus of claim 13, further comprising a source of pressurized gas connected to a channel formed in said block so as to intersect said passage between said first and second planar sealing members.

* * * * *

UNITED STATES PATENT AND TRADEMARK OFFICE
CERTIFICATE OF CORRECTION

PATENT NO.  : 5,709,840
DATED       : January 20, 1998
INVENTOR(S) : David L. Juranas It is certified that error appears in the above-identified patent and that said Letters Patent is hereby corrected as shown below:

Claim 13(g), replace the present language with: "wherein said tube is positioned in a manner enabling said tube to be used for adding components to and removing components from a reactor flask into which said tube extends."

Signed and Sealed this

Ninth Day of June, 1998

*Attest:*

BRUCE LEHMAN

*Attesting Officer*          Commissioner of Patents and Trademarks